United States Patent [19]

Plattier et al.

[11] 4,115,326

[45] Sep. 19, 1978

[54] PERFUMING OF COMPOSITION USING 3-(10-UNDECENYLOXY)PROPRIONITRILE

[75] Inventors: Marcel Plattier, Antibes; Paul José Teisseire, Grasse, both of France

[73] Assignee: Societe Anonyme Roure Bertrand Dupont, Paris, France

[21] Appl. No.: 717,281

[22] Filed: Aug. 24, 1976

[30] Foreign Application Priority Data

Sep. 4, 1975 [CH] Switzerland ............... 11436/75

[51] Int. Cl.$^2$ .................. C07C 121/34; A61K 7/46
[52] U.S. Cl. ................... 252/522; 260/465.6; 252/89 R; 252/174; 424/69; 424/358
[58] Field of Search ............ 260/465.6; 252/522

[56] References Cited

U.S. PATENT DOCUMENTS 2,280,790  4/1942  Bruson ................. 260/465.6

OTHER PUBLICATIONS

Kulesza, et al., C.A., 84, (1976), 8841e.
Gaiffe, et al., C.A., 67, (1967), 73110d.

Primary Examiner—Joseph Paul Brust
Attorney, Agent, or Firm—Wallenstein, Spangenberg, Hattis & Strampel

[57] ABSTRACT

A novel nitrile 3-(10-undecenyloxy)propionitrile is disclosed having remarkable odoriferous properties and being useful in a variety of compositions and formulations. A process for the preparation of said nitrile is also disclosed.

2 Claims, No Drawings

PERFUMING OF COMPOSITION USING 3-(10-UNDECENYLOXY)PROPRIONITRILE

DETAILED DESCRIPTION OF THE INVENTION

The present invention relates to a novel nitrile 3-(10-undecenyloxy)propionitrile, having the formula:

$$CH_2=CH-(CH_2)_9-O-(CH_2)_2CN$$

This novel compound has a slightly fruity odour reminiscent of pineapple. The odour also has a salicylic aspect and a generally powdery character; it also has exceptional tenacity. In addition, it may be used to improve the odour of certain synthetic products. One of its main uses is in the modification of basic notes and it may thus with advantage be employed in compositions having a powdery note. The nitrile is stable in both alkaline and acid media. These characteristic odorant and chemical properties enable the compound of the present invention to be used in perfumery, for example for the preparation of perfumes or to perfume products of all types, such as cosmetic articles, e.g. soaps, powders, creams and lotions. The amount of the compound of the invention which may be used in odorant compositions depends on the use and can vary over a wide range, for example between 0.1 and 30% by weight. A preferred range is between 1.0 and 15% by weight. In order to perfume soaps, it is generally sufficient to incorporate 1 to 5% of the compound of the invention.

The compound of the invention may be prepared by a process which comprises reacting 10-undecen-1-ol with acrylonitrile preferally in the presence of a basic catalyst. This catalyst can be sodium or potassium or an alcoholate thereof. Preferred alcoholates include methoxides and ethoxides. The amount of catalyst employed may vary between 1% and 5% by weight of the undecenol used. The reaction may be carried out at any convenient temperature. Preferably the reaction is effected at reflux. However, lower temperatures down to about 30° C may be used although at such temperatures the reaction time will be increased. At reflux temperatures the reaction proceeds fairly swiftly (e.g. 1 hour) but will take up to about 24 hours if temperature of as low as 30°-40° C is used. The reaction may be effected in the presence of an inert organic solvent.

The invention will now be illustrated with reference to the following Examples. Example 1 describes the preparation of the novel substance of the invention, Examples 2 and 3 describe perfume formulations and Examples 4 and 5 describe perfumed cosmetic articles containing the novel compound of the invention.

EXAMPLE 1

A 2 liter reactor provided with a stirrer, a heater, a reflux condenser and a 1 litre collecting flask was charged with 850 g of 10-undecen-1-ol and then 2 g of sodium and heated to 90°-95°. When the sodium had completely reacted, the reaction mass was cooled to 80° and 132.5 g of acrylonitrile were added at 80° in the course of ½ hour. The mass was maintained at this temperature for a further hour and then cooled to 25° and 20 ml of acetic acid and then 1 liter of benzene were added. The organic phase was decanted off and then washed 3 times with 250 ml of water. The solvent was finally distilled off in a water bath under a pressure of 30 mm Hg. 1006 g of crude 3-(10-undecenyloxy)propionitrile were obtained, which were fractionated under a pressure of 0.5 mm Hg. 432.7 g of pure nitrile were collected, which represents a theoretical yield of 77.6% with respect to acrylonitrile, 38.8% with respect to undecenol employed and 81.1% with respect to undecanol consumed. The pure 3-(10-undecenyloxy)propionitrile had the following physical constants; B.p./0.5 = 116°, $n_D^{15}$ = 1.4528.

EXAMPLE 2

| (Rose perfume) | Parts by weight |
| --- | --- |
| Citronellol extra | 15 g |
| Geraniol | 5 g |
| Geranyl acetate | 2.50 g |
| Hydroxydihydrocitronellal | 10 g |
| Phenylethyl alcohol | 10 g |
| Metol acetate | 2.50 g |
| Extra white alpha ionantheme | 2.50 g |
| Guaiol acetate | 5 g |
| Nerol petals | 2.50 g |
| Trichlormethylphenylcarbinol acetate | 5 g |
| 3-(10-undecenyloxy)propionitrile | 5 g |
| Total | 65 g |

EXAMPLE 3

| (Fern perfume) | Parts by weight |
| --- | --- |
| Lavander 40% | 20 g |
| Coumarin | 20 g |
| Patchouli | 20 g |
| Vetiver bourbon | 10 g |
| Heliotropin | 10 g |
| Vanillal containing 10% ethyl phthalate | 20 g |
| Amyl salicylate | 40 g |
| Resinoid oak moss A No. 1 (50% solution in ethyl phthalate) | 40 g |
| 12-oxahexadecanolide | 10 g |
| Geranium bourbon | 10 g |
| Resinoid benzoin No. 1 syrup 50% | 40 g |
| 3-(10-undecenyloxy)propionitrile | 8 g |
| Total | 248 g |

EXAMPLE 4

A bar of toilet soap composed of 97 g of soap (prepared from a mixture of 70% beef fat, 25% Ceylon coconut oil and 5% lard) and 3 g of the composition of Example 2 is prepared.

This bar of toilet soap gave off a particularly intense rose odour in which the floral and fresh characteristics were enhanced.

EXAMPLE 3

A concentrated liquid detergent composed of:

| Sodium alkylbenzenesulphonate | 600.0 g |
| --- | --- |
| Sodium lauryl sulphonate | 30.0 g |
| Water | 170.0 g |
| Fern composition of Example 3 | 1.6 g | was prepared.

This detergent had a particularly pleasant woody, coumarin, fruity odour.

What is claimed in:

1. A process for perfuming compositions wherein 3-(10-undecenyloxy) propionitrile having the formula $$CH_2=CH-(CH_2)_9-O-(CH_2)_2CN$$

is added to the compositions in proportions of from 0.1 to 30%, by weight, of said compositions.

2. A perfumed composition containing from 0.1 to 30%, by weight of said composition, of the compound 3-(10-undecenyloxy) propionitrile having the formula $$CH_2=CH-(CH_2)_9-O-(CH_2)_2CN$$

as an odorant.

* * * * *